(12) United States Patent
Kunuki

(10) Patent No.: US 7,939,023 B2
(45) Date of Patent: May 10, 2011

(54) ASSAY APPARATUS AND SENSOR HOLDING METHOD

(75) Inventor: Yoshiyuki Kunuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1045 days.

(21) Appl. No.: 11/729,888

(22) Filed: Mar. 30, 2007

(65) Prior Publication Data

US 2007/0231210 A1    Oct. 4, 2007

(30) Foreign Application Priority Data

Mar. 30, 2006  (JP) ................. 2006-095183

(51) Int. Cl.
```
G01N 21/64     (2006.01)
G01N 27/16     (2006.01)
G01N 21/00     (2006.01)
C12M 1/34      (2006.01)
G01N 35/00     (2006.01)
G01N 1/10      (2006.01)
```
(52) U.S. Cl. ........... 422/82.08; 422/63; 422/64; 422/65; 422/68.1; 422/82.11; 422/104; 435/287.1; 435/288.4; 435/288.5; 436/46; 436/47; 436/48; 436/52; 436/164; 356/246; 356/445

(58) Field of Classification Search ................ None
See application file for complete search history.

(56) References Cited

U.S. PATENT DOCUMENTS 5,164,589 A    11/1992   Sjodin
5,313,264 A    5/1994    Ivarsson et al.

FOREIGN PATENT DOCUMENTS

JP          3294605 B        5/2002

*Primary Examiner* — Sean E Conley
*Assistant Examiner* — Neil Turk
(74) *Attorney, Agent, or Firm* — Sughrue Mion, PLLC

(57) ABSTRACT

A sensor unit is retained on an assay stage of a surface plasmon resonance (SPR) assay apparatus. The sensor unit includes a prism having a sensing surface, disposed on an upper surface thereof, for detecting reaction of a sample. A flow cell is secured to the upper surface, and has a flow channel for flow of sample fluid containing the sample to the sensing surface. The sensor unit is set removably on the assay apparatus for optically measuring reaction of the sample. In sensor holding, the sensor unit is set on a stage surface of the assay stage by directing down the prism. In a pushing step, a lower surface of the prism is pushed on the stage surface in a first direction upright relative to the stage surface. Two holders push an upper face of the first and second ridges of the prism in the first direction.

15 Claims, 11 Drawing Sheets

ASSAY APPARATUS AND SENSOR HOLDING METHOD

BACKGROUND OF THE INVENTION

1. Field of the Invention

The present invention relates to an assay apparatus and sensor holding method. More particularly, the present invention relates to an assay apparatus and sensor holding method, in which a sensor unit can be positioned reliably without offset or change in moving a pipette device.

2. Description Related to the Prior Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. Nos. 5,164,589 and 5,313,264 (corresponding to JP-B 3294605) disclose an SPR assay apparatus with Kretschmann configuration. In the assay apparatus, the sensing surface is positioned opposite to an interface where a metal thin film is connected with a prism as dielectric block. Light is applied through the prism to the sensing surface. Total reflection of the illuminating light occurs. Reaction of samples is assayed by detecting the SPR on the sensing surface.

Biomaterials as samples are handled as sample fluid which contains a sample and fluid medium to which the sample is added, for the purpose of preventing modification or deactivation due to drying. Examples of fluid media include physiological saline water, pure water, buffer liquids and the like. The assay apparatus of U.S. Pat. Nos. 5,164,589 and 5,313,264 (corresponding to JP-B 3294605) is used to detect and study interaction between biomaterials. The flow channel is formed for flow of the sample fluid in contact with the sensing surface. A flow cell with a flow channel and the prism are disposed on an assay stage of the assay apparatus. A sensor unit of a chip type is set on the assay stage, having thin film of metal formed on a glass substrate.

In U.S. Pat. Nos. 5,164,589 and 5,313,264 (corresponding to JP-B 3294605), a pump is connected with the flow channel by a conduit, valve and the like, to supply the flow channel with the sample fluid from a fluid reservoir. However, a problem of contamination is likely to occur in that the sample may stick on the inside of the conduit and will mix with the sample fluid.

To solve such a problem, a type of the assay apparatus is suggested in which pipette devices are used. Each of the pipette devices includes a pipette head and a pipette tip secured to the pipette head removably. The pipette devices dispense the sample fluid into the flow channel. It is possible in the assay apparatus with the pipette devices to prevent contamination in introducing the sample fluid into the flow channel by replacing pipette tips each time that the fluid is changed over.

The sensor unit for use in the assay apparatus with the pipette devices includes a flow cell, the prism and a connection mechanism. The flow cell has the flow channel. The prism is overlaid with the thin film of metal. The sensor unit connects a flow cell with the prism by positioning the flow channel on the thin film. A flow channel is a conduit extending through a flow cell in an U shape. Orifices are formed at ends of the flow channel and open in the upside of the flow cell. A lower portion of the flow channel is open, and is closed by a thin film of metal. Therefore, fluid can contact the thin film on the flow channel by introducing the fluid into the flow channel. If a pipette device is used for dispensing the fluid into the flow channel, a tip of the pipette device is inserted in an end of the flow channel, so as to introduce the fluid being stored by aspiration in the pipette device.

However, it is likely in the assay apparatus with the pipette devices to create errors in measurement by incidentally shifting the sensor unit in loading or unloading the pipette devices on the flow channel. Such errors in the position of the sensor unit will change the position of the reflected light in the photo detector. Even if analysis according to a measuring signal and a reference signal is carried out, the error cannot be removed.

If a sensor unit is a multi channel type having a plurality of sensing surface and the flow channel associated therewith, samples on the sensing surfaces can be assay at the same time. However, the problem is further serious in high force exerted to the sensor unit upon loading and unloading the pipette device, because of the greater number of the pipette devices according to the number of the flow channel.

SUMMARY OF THE INVENTION

In view of the foregoing problems, an object of the present invention is to provide an assay apparatus and sensor holding method, in which a sensor unit can be positioned reliably without offset or change in moving a pipette device.

In order to achieve the above and other objects and advantages of this invention, an assay apparatus in which a sensor unit is used is provided. The sensor unit includes an optical block having a sensing surface, disposed on an upper surface thereof, for detecting reaction of a sample, and a flow cell, secured to the upper surface, having a flow channel for flow of sample fluid containing the sample to the sensing surface, wherein light is applied to the optical block and received upon reflection thereon, for optically measuring reaction of the sample on the sensing surface. The assay apparatus includes an assay stage, having a stage surface for contacting a lower surface of the optical block, for supporting the sensor unit removably. An optical block retaining mechanism retains the sensor unit in a predetermined orientation on the stage surface by engagement with the optical block. The optical block retaining mechanism includes a holder, shiftable between a retaining position and an initial position, for, when in the retaining position, pushing the lower surface of the optical block on the stage surface, and for, when in the initial position, releasing the optical block from retention on the stage surface, the holder exerting force of pushing to the optical block in a first direction which is upright relative to the stage surface.

Furthermore, there is a fluid dispenser having a pipette device. The pipette device moves down in the first direction to access to the flow cell, and introduces the sample fluid when set at the flow channel.

Plural sensing surfaces are arranged in the sensor unit in a sensor longitudinal direction, plural flow channels are arranged in the sensor unit and correspond to the sensing surfaces, and plural pipette devices of the fluid dispenser access to the flow channels.

The optical block includes first and second engageable portions formed to protrude from or retreat in respectively lateral faces thereof. The holder is at least two holders so positioned that the stage surface is located between, for pushing an upper face of the first and second engageable portions in the first direction.

Furthermore, a flow cell holder accesses downwards to the flow cell of the sensor unit on the stage surface, and for pushing an upper surface thereof to press the flow cell on the optical block.

Pushing of the optical block retaining mechanism and the flow cell holder is started after transfer of the sensor unit to the assay stage is completed.

The at least two holders are at least four holders arranged in first and second arrays extending from a first end of the optical block to a second end thereof as viewed in the sensor longitudinal direction thereof.

The holders are shiftable independently from one another.

Furthermore, a cam follower is secured to the holder. A cam surface constitutes a cam mechanism, and drives the cam follower to shift the holder.

The cam mechanism includes a motor. A cam shaft has the cam surface on a shaft surface thereof, for being rotated by the motor, and for driving the cam follower.

Furthermore, a biasing mechanism biases the holder toward the retaining position.

The cam mechanism includes a motor. A cam plate has the cam surface with an inclination, for being slid by the motor, and for driving the cam follower.

The cam surface is so disposed that a clearance from the cam follower occurs when the holder reaches the retaining position.

The flow cell holder includes a pad panel opposed to the upper surface of the flow cell. A cam surface is formed with an upper portion of the pad panel, and having an inclination. A cam projection pushes the cam surface by moving, to shift the pad panel toward the flow cell.

Furthermore, a cushion mechanism reduces shock between the flow cell holder and the flow cell at a time of pushing.

The optical block retaining mechanism further includes a horizontal holder for pushing a first lateral face of the optical block in a second direction which is along the stage surface, to set a second surface of the optical block on a reference surface on the assay stage for holding in the second direction.

The sensor unit moves in the sensor longitudinal direction for transfer to the assay stage, and the sensor longitudinal direction is crosswise to the first direction and to the second direction.

The horizontal holder is supported on the holder, and starts retention in the second direction together with the holder.

Also, a sensor holding method of retaining a sensor unit on an assay stage of an assay apparatus is provided. The sensor unit includes an optical block having a sensing surface, disposed on an upper surface thereof, for detecting reaction of a sample, and a flow cell, secured to the upper surface, having a flow channel for flow of sample fluid containing the sample to the sensing surface, the sensor unit being set removably on the assay apparatus for optically measuring reaction of the sample. The sensor holding method includes a setting step of setting the sensor unit on a stage surface of the assay stage by directing down the optical block. In a pushing step, a lower surface of the optical block is pushed on the stage surface in a first direction which is upright relative to the stage surface.

Furthermore, an assay apparatus in which a sensor unit is used is provided. The sensor unit includes an optical block for constituting a sensor platform, of which one surface is a reflection surface for reflecting light applied thereto, the sensor platform including a sensing surface, positioned to extend along the reflection surface, for reaction of a sample, and a flow cell, having a flow channel for flow of the sample to the sensing surface. The assay apparatus includes an assay stage, having a stage surface for contacting a first surface of the optical block, for supporting the sensor unit removably. An optical block retaining mechanism retains the sensor unit in a predetermined orientation on the stage surface by engagement with the optical block. The optical block retaining mechanism includes a holder, shiftable between a retaining position and an initial position, for, when in the retaining position, pushing the first surface of the optical block on the stage surface, and for, when in the initial position, releasing the optical block from retention on the stage surface, the holder exerting force of pushing to the optical block in a first direction which is upright relative to the stage surface.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
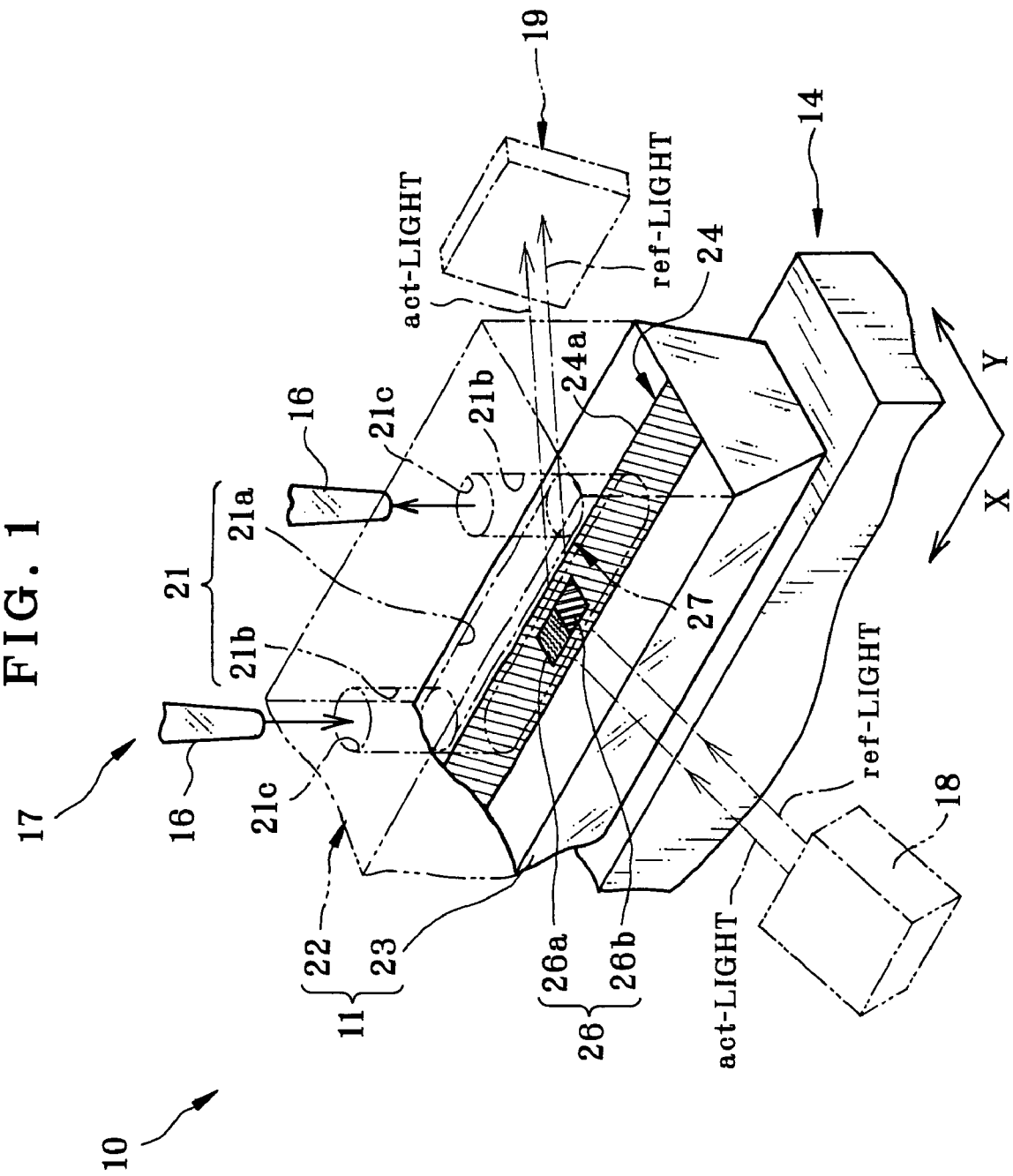
FIG. 1 is a perspective view illustrating a surface plasmon resonance (SPR) assay method.

In FIG. 1, a sensor unit 11 is for use in a surface plasmon resonance (SPR) assay apparatus 10 to assay reaction of analyte or sample. The assay apparatus 10 includes an assay stage 14, an assay optical unit, and a fluid dispenser or dispensing head 17. The assay optical unit applies light to the sensor unit 11 and receives the light reflected by the sensor unit 11 for photo detection. The fluid dispenser 17 includes a plurality of pipette devices 16 for introduction and removal of liquid with the sensor unit 11. The assay optical unit includes a light source 18 for generating illuminating light and a photo detector 19 for photo detection to output an SPR signal.

The sensor unit 11 includes flow cell 22 and a prism 23, which is an example of an optical block. A flow channel 21 is formed in the flow cell 22 for flow of fluid. The prism 23 constitutes a sensor platform, receives light emanated by the light source 18, and reflects the light toward the photo detector 19. A lower surface of the flow cell 22 is opposed to and pressed on the upside of the prism 23. The flow channel 21 is in a U shape and includes a passageway 21a and conduit zones 21b. The passageway 21a causes fluid to flow on the upside of the prism 23. The conduit zones 21b extend from ends of the passageway 21a to the upside of the flow cell 22. Orifices 21c are upper ends of the conduit zones 21b and open for insertion of pipette tips of the pipette devices 16 to dispense and remove fluid.

The pipette devices 16 are operated alternately with one another. For example, a first one of the pipette devices 16 operates for dispensation while a second one of those operates for aspiration. Fluid, after being dispensation through the first one at a first one of the orifices 21c, is drawn and removed through the second pipette device at a second one of the orifices 21c.

A diameter of the flow channel 21 is approximately 1 mm. An interval between the orifices 21c is approximately 10 mm. The passageway 21a is a space formed in a lower face of the flow cell 22. An upside of the prism 23 for contact with this covers the space. The flow cell 22 is formed from elastic material in a manner of sealant which tightens the closing of the space by resilient deformation by pressure.

A thin film 24 of metal is formed on an upper surface of the prism 23 by vapor deposition. A first surface of the thin film 24 is a sensing surface 24a. The thin film 24 constitutes a sensor platform in a strip shape, and is opposed to the flow channel 21 formed in the flow cell 22. A linker film 26 is formed on the sensing surface 24a. The linker film 26 is a ligand immobilizing film for immobilizing ligand for contact with analyte in the flow channel 21. The linker film 26 is formed at the time of producing the sensor unit 11. Sensor cells 27 are constituted by the flow channel 21 and the sensing surface 24a having the linker film 26.

There are a measuring region (act) 26a and a reference region (ref) 26b formed on the linker film 26. The measuring region 26a is used for immobilizing ligand for reaction of analyte and ligand. The reference region 26b remains without immobilization of ligand, and used for obtaining a reference signal in the assay of the measuring region 26a. The reference region 26b is formed upon producing the linker film 26. Specifically, the linker film 26 is subjected to surface processing, so as to deactivate a reaction group bindable with ligand in a partial region that is half as large as the entirety of the linker film 26. Thus, a first half of the linker film 26 is the measuring region 26a. A second half of the linker film 26 is the reference region 26b.

At first, ligand fluid is caused to flow to the linker film 26 through the flow channel 21, to immobilize ligand on the measuring region 26a. This is a sample immobilizing flow before setting of the sensor unit 11 on the assay stage 14. After the immobilization, the analyte fluid with analyte is introduced to the linker film 26 through the flow channel 21, to cause the analyte to contact the ligand. An assay signal is obtained and read, to measure interaction or binding of the ligand and analyte.

For the assay of interaction between an analyte and ligand, at first, liquid buffer is introduced into the flow channel 21, and caused to flow continuously for a prescribed time. After this, analyte solution or analyte fluid, as a fluid which contains analyte and fluid medium that may be solvent, is introduced into the flow channel 21. Then liquid buffer is introduced again. Note that the flow channel 21 may be cleaned or washed before initially introducing the liquid buffer. Reading of an SPR signal in a photo detector starts upon initially introducing the liquid buffer in order to detect a reference level of a signal. The reading is continued until the introduction of the liquid buffer at the second time after entry of analyte fluid. It is possible not only to detect the reference level or a baseline level, but to assay interaction or reaction between the analyte and the ligand, and to measure a signal until dissociation between the analyte and ligand in response to introduction of the liquid buffer. Introduction and removal of the liquid buffer and the analyte fluid are carried out by loading and unloading the pipette devices 16 in the flow channel 21.

The light source 18 applies light to a reflection surface or interface 30 defined between the prism 23 and the thin film 24 through the prism 23. As reaction between the ligand and analyte is expressed by a change in the resonance angle. The light source 18 applies light beams to the interface 30 at various incident angles satisfying the total reflection condition. The light source 18 includes a light source device and an optical system. Examples of the light source devices include a light emitting diode (LED), laser diode (LD), super luminescent diode (SLD), and other light emitting element.

The optical system includes a collimator lens, fiber optics, a condenser lens and the like. The collimator lens collimates light from the light source. The fiber optics receive parallel light from the collimator lens, and emanate diffused light. The condenser lens receives the diffused light, and condenses the light in a specific position on the interface 30. Thus, light beams of various angles are applied to the interface 30. The single light source illuminates the measuring region 26a and the reference region 26b with act light and ref light. To this end, a single light source device is used with an additional prism for splitting light from the light source device into two paths. Alternatively, two light source devices may be arranged and used.

An example of the photo detector 19 is a CCD area sensor or an array of photo diodes. Light reflected by the interface 30 is received by the photo detector 19 to output an assay signal at a level according to the intensity of the reflected light. Rays of light are incident upon the interface 30 at various angles. The light is reflected by the interface 30 at various angles of reflection according to the angles of the incidence. The photo detector 19 receives reflected light of plural angles, converts the same photoelectrically, to output an SPR signal at a level of the light intensity. The signal from the photo detector 19 is sent to a data analyzer (not shown). Reaction is assayed by analyzing attenuation of light according to data processing of the signal in the data analyzer.

Figure 2:
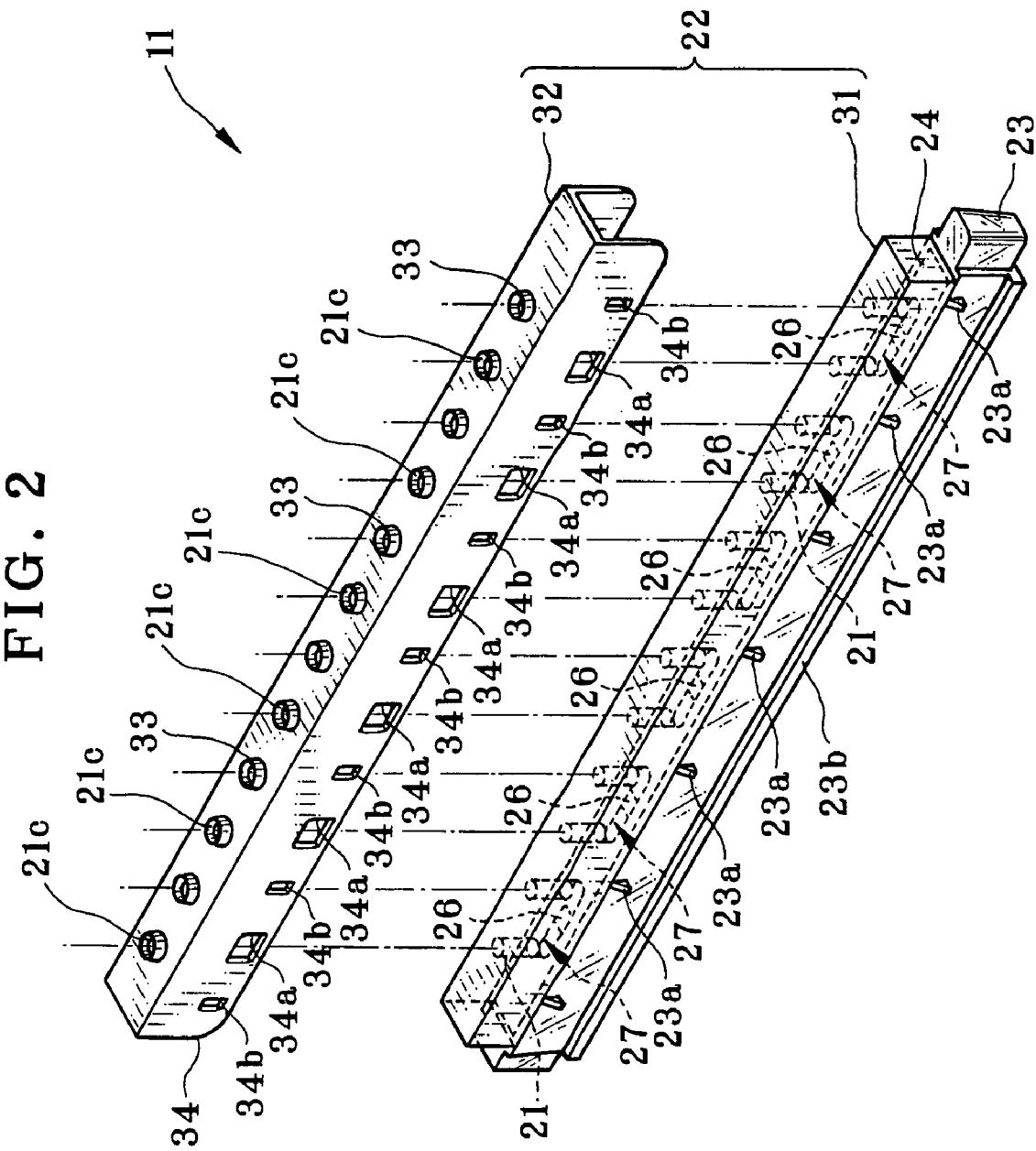
FIG. 2 is an explanatory view in perspective illustrating a sensor unit.

In FIG. 2, the sensor unit 11 has a long shape having the six sensor cells 27. A multi channel form of the sensor unit 11 having the sensor cells 27 is advantageous in high efficiency in the assay. This is because assay with the sensor cells 27 is possible only by setting the single sensor unit 11 on the assay stage 14. Operation of loading and unloading of the sensor unit 11 with the assay stage 14 is smaller than if the sensor cell is single in the sensor unit 11. Note that the number of the sensor cells 27 in the sensor unit 11 may be five or less, or seven or more despite the embodiment.

While the sensor unit 11 is set in the assay stage 14, the six sensor cells 27 in the assay apparatus 10 are simultaneously used for assay. Light beams, namely act-light and ref-light, are applied to each of the sensor cells 27 by the light source 18. The photo detector 19 receives reflected light beams from the sensor cells 27 at the same time, to output an SPR signal for each of the sensor cells 27.

The flow cell 22 is in a form of a quadrilateral prism, and formed from elastic material. The flow cell 22 includes a flow cell body 31 having the flow channels 21, and a flow cell cover 32 formed together with the flow cell body 31. The number of the flow channels 21 is six (6) in the flow cell 22. The flow channels 21 are arranged at a regular interval in the longitudinal direction. A lower surface of the flow cell body 31 contacts the upside of the prism 23.

Figure 3:
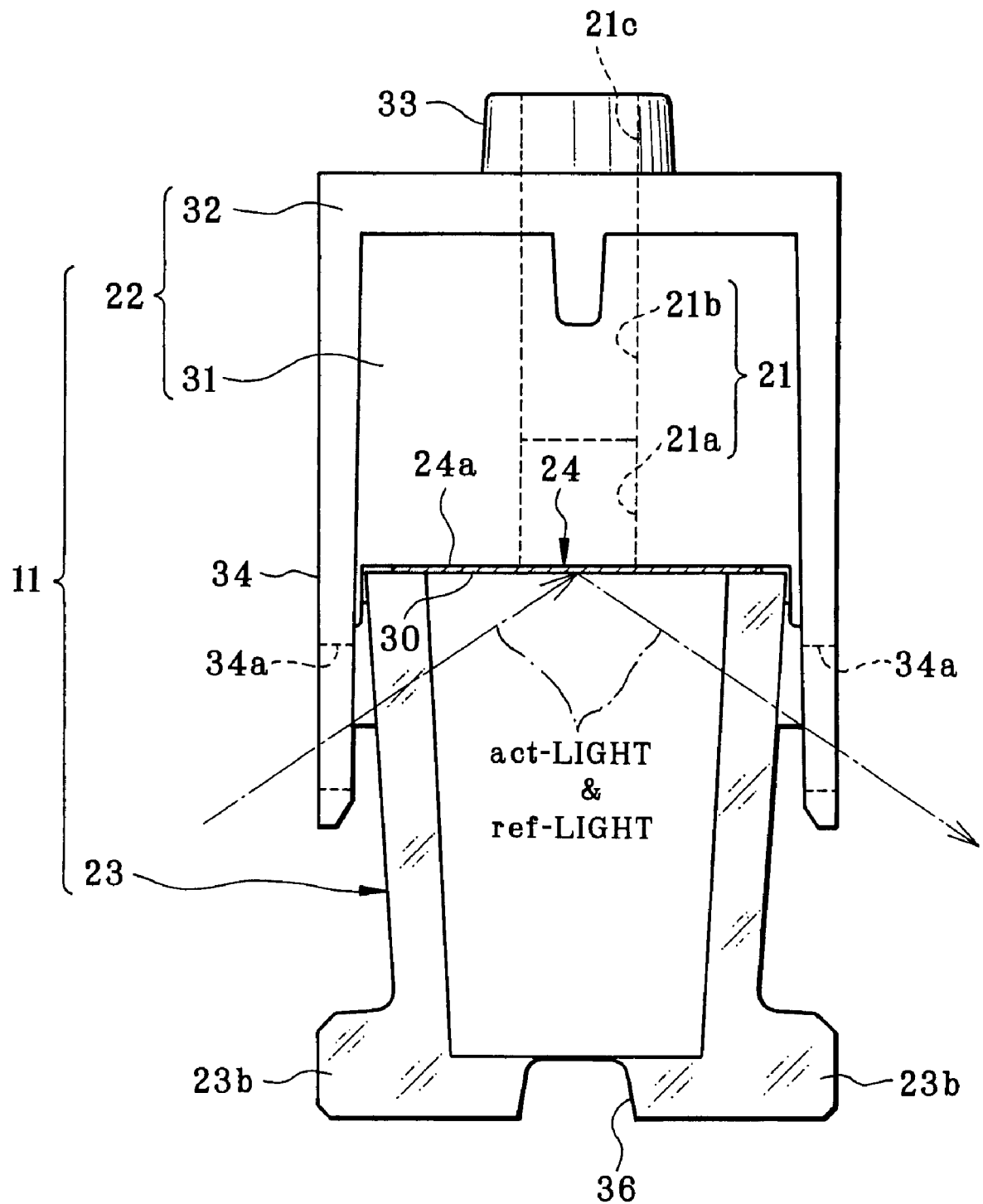
FIG. 3 is a front elevation illustrating the sensor unit.

In FIG. 3, the flow cell cover 32 extends in a channel shape to cover an upper face and lateral faces of the flow cell body 31. Ring shaped bosses 33 are formed on an upper face of the flow cell cover 32 to protrude upwards as well as the orifices 21c of the flow channel 21. The two orifices 21c are associated with each of the sensor cells 27. The number of the ring shaped bosses 33 is 12 and arranged in the longitudinal direction of the flow cell. 12 pipette devices 16 are arranged in the fluid dispenser 17, and include six dual pipette assemblies according to the number of the sensor cells 27. See FIG. 4. The fluid dispenser 17 accesses the ring shaped bosses 33 downwards to the sensor unit 11, and inserts its pipette tips into the orifices 21c of the flow channel 21.

Flow cell skirt panels 34 are formed to project downwards from edges of the flow cell cover 32. The flow cell skirt panels 34 cover the upper portions of the lateral faces of the prism 23. Should scratches, dust or fingerprints be created on the upper portions of the lateral faces, diffuse reflection will occur because of positions of light paths, to lower precision in the assay. In the embodiment, the flow cell skirt panels 34 protect the prism 23 from occurrence of such scratches, dust or fingerprints. Path openings 34a are formed in the flow cell skirt panels 34 and positioned for respectively the sensor cells 27. Retaining holes 34b are formed in the flow cell skirt panels 34 and between the path openings 34a for engagement with the prism 23.

The prism 23 is in a shape of a quadrilateral prism, and when viewed in a cross section, in a shape of a trapezoid. Various materials can be used for forming the prism 23, the examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like. The thin film 24 extends in the longitudinal direction of the prism 23 on its reflection surface as interface 30. The linker film 26 is positioned for each of the flow channel 21.

Retaining claws 23a are formed to project from lateral faces of the prism 23 and engageable with the retaining holes 34b of the flow cell 22. The retaining claws 23a are positioned at the retaining holes 34b. The flow cell 22 is kept fixed on the prism 23 by the retaining claws 23a. Engageable ridges 23b are formed on edges of a lower face of the prism 23 and protrude horizontally. The engageable ridges 23b extend in a longitudinal direction of the prism 23. As will be described in detail, a retaining mechanism is incorporated in the assay apparatus 10 for retaining the sensor unit 11 on the assay stage 14. The engageable ridges 23b receive engagement of the retaining mechanism. A guide channel 36 is formed in a lower face of the prism 23 and extends longitudinally. To transfer the sensor unit 11 to the assay stage 14, the guide channel 36 is engaged with a rail (not shown) of the assay apparatus 10 to guide the movement of the sensor unit 11.

Figure 4:
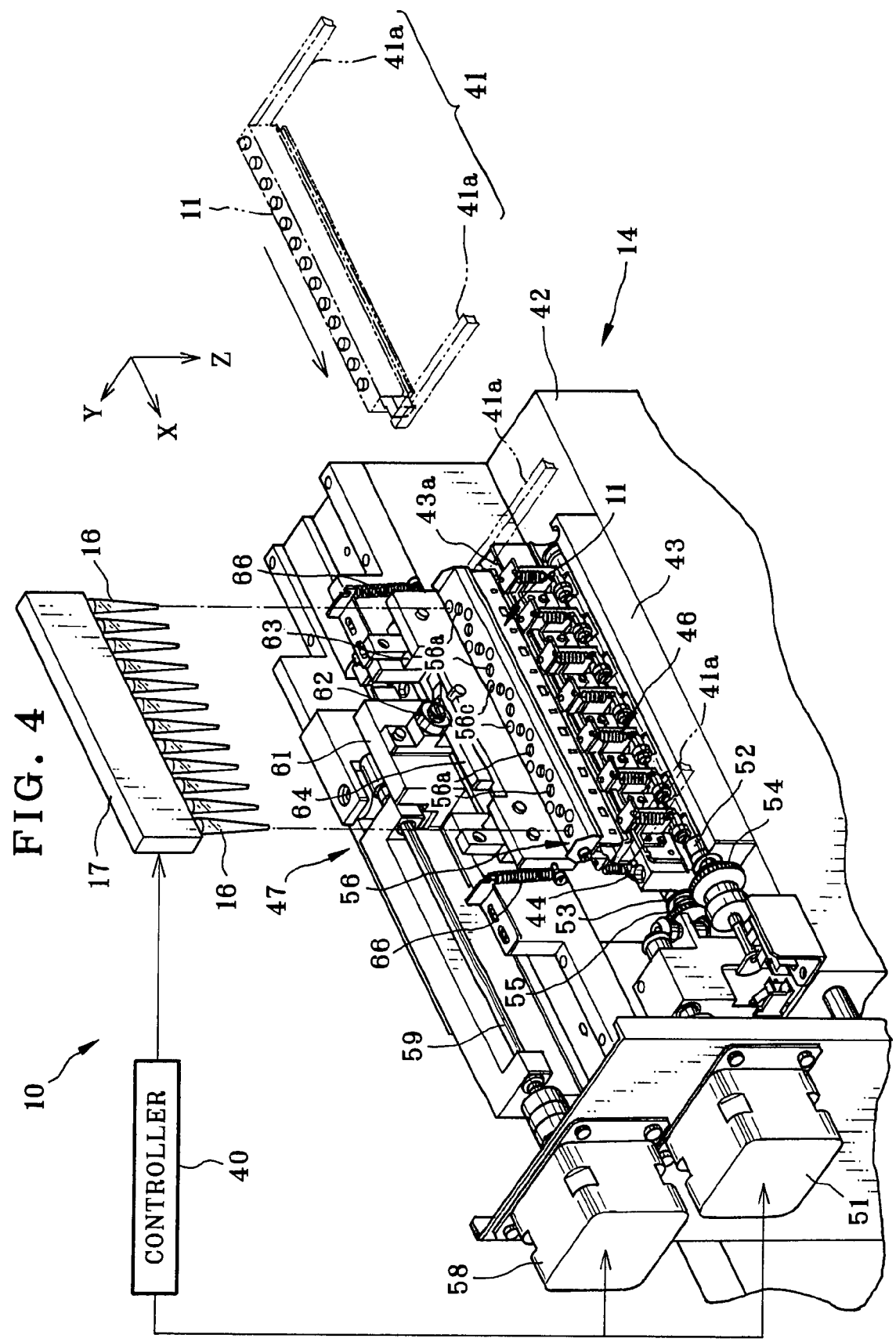
FIG. 4 is a perspective view illustrating an assay stage.

In FIG. 4, a controller 40 is incorporated in the assay apparatus 10. The controller 40 controls various elements including the fluid dispenser 17, a handling mechanism, a sensor retaining mechanism and the like for actuation and time points of actuation.

A handling mechanism transfers the sensor unit 11 to the assay stage 14. In the transfer, the sensor unit 11 is longitudinally directed in the direction of the X axis which is perpendicular to the Z axis of the direction of the access of the pipette devices 16 to the flow channel 21. In the handling mechanism, a handler or handling head 41 has a couple of handling arms 41a which nip and hold the sensor unit 11 in the longitudinal direction. The sensor unit 11 is transferred to and set in the assay stage 14 while held in the handler 41, and subjected to assay. After the assay, the sensor unit 11 is moved away from the assay stage 14 by the handler 41.

The assay stage 14 includes a stage support 42 and a rack or stage platform 43. The rack 43 is disposed on the stage support 42, and has a stage surface 43a for placing the sensor unit 11. A stopper 44 projects from the stage surface 43a for limiting advance of the sensor unit 11 in the direction of the X axis by contacting an end of the sensor unit 11. The stopper 44 precisely positions the sensor unit 11 in the direction along the X axis. A sensor retaining mechanism is disposed on the stage support 42 for holding the sensor unit 11 on the stage surface 43a.

The fluid dispenser 17 moves up and down along the Z axis for moving the pipette devices 16 relative to the flow channel 21. External force in the direction of the axis Z is applied to the sensor unit 11 in the loading and unloading the pipette devices 16. Should offsetting of the position and a change in the orientation of the sensor unit 11 be occur upon application of external force in the direction of the Z axis, precision in the assay will be low. Handling will be influenced after the assay to move the sensor unit 11 away from the assay stage 14. However, a plurality of the sensor cells 27 are assayed in the assay apparatus 10 at the same time. Loading and unloading of the pipette devices 16 on the sensor cells 27 is simultaneous, so that external force in the direction of the X axis is higher than that in assay of only one of the sensor cells 27 at a time. Thus retention force must be high in consideration of the external force.

The sensor retaining mechanism includes a prism retaining mechanism 46 as optical block retaining mechanism, and a flow cell holder or pusher 47. The prism retaining mechanism 46 is engaged with the prism 23 for keeping the sensor unit 11 oriented and positioned in a predetermined manner. The flow cell holder 47 presses the flow cell 22 in the direction along the Z axis for pressing the flow cell 22 against the prism 23. The prism retaining mechanism 46 is engaged with the engageable ridges 23b of the prism 23 for retention in the direction of the Z axis, to position the lower face of the prism 23 on the stage surface 43a. Also, the prism retaining mechanism 46 positions the prism 23 in the width direction along the Y axis which is perpendicular to the X axis and to the Z axis.

After the sensor unit 11 is transferred to the assay stage 14, the controller 40 causes the prism retaining mechanism 46 to hold the prism 23. After this, the flow cell holder 47 is driven to push the flow cell 22. It is likely upon the reach of the sensor unit 11 to the assay stage 14 that the sensor unit 11 is not properly oriented, for example the sensor unit 11 may be inclined rotationally about the X axis. If the flow cell 22 is pushed during the inclination of the lower surface of the prism 23 relative to the stage surface 43a, the sensor unit 11 may be inclined further, or may fall down finally. In the embodiment, the prism 23 is retained at first to keep the sensor unit 11 oriented properly. In this state, the flow cell holder 47 is driven for pushing.

After the assay, the controller 40 releases the retention of the prism retaining mechanism 46, and then releases the retention of the flow cell holder 47. As will be described later, force is exerted to the prism 23 in a direction to incline the sensor unit 11 rotationally about the X axis. During the exertion of the force, retention with the flow cell holder 47 is continued to prevent the sensor unit 11 from changing in the orientation.

A driving mechanism for the prism retaining mechanism 46 includes a motor 51 and cam shafts 52 and 53. The cam shafts 52 and 53 are rotated by the motor 51 to drive the prism retaining mechanism 46. Gears 54 and 55 are positioned at ends of the cam shafts 52 and 53, and meshed with one another. At first, rotation of the motor 51 is transmitted to the cam shaft 52, which causes the gears 54 and 55 to rotate the cam shaft 53. Supports are formed in a lower portion of the rack or stage platform 43 for supporting the cam shafts 52 and 53 in a rotatable manner.

A pressing pad panel 56 is included in the flow cell holder 47, and presses the flow cell 22 in the direction of the Z axis to push the lower face of the flow cell 22 on the upside of the prism 23. The pad panel 56 is movable up and down along the Z axis and between a retaining position to push the flow cell 22 on the prism 23 and an initial position away from the retaining position. A size of the pad panel 56 is large enough to cover the entire upper face of the flow cell 22. Insertion holes 56a are formed in the pad panel 56 for passage of the pipette devices 16, and allow the pipette devices 16 to access the flow channel 21.

A driving mechanism for the pad panel 56 includes a motor 58, a transmission shaft 59 and a carriage 61. A gear train (not shown) is caused by the transmission shaft 59 to transmit rotation of the motor 58 to the carriage 61. A rotatable cam projection or wheel 62 is secured to a front of the carriage 61. A cam surface 64 to be described later is engaged with the cam wheel 62. The carriage 61 is caused by rotation of the transmission shaft 59 to slide horizontally along the X axis together with the cam wheel 62. The cam wheel 62 is rotatable on the carriage 61 for reduced friction with the cam surface 64.

A pad panel support 63 supports the pad panel 56. The pad panel support 63 is movable from the stage support 42 up and down together with the pad panel 56. Tension coil springs 66 are secured to ends of the pad panel 56, and bias the pad panel 56 and the pad panel support 63 upwards in a direction away from the flow cell 22. In an initial state, the pad panel 56 is set in the upper position by the bias.

Figure 5:
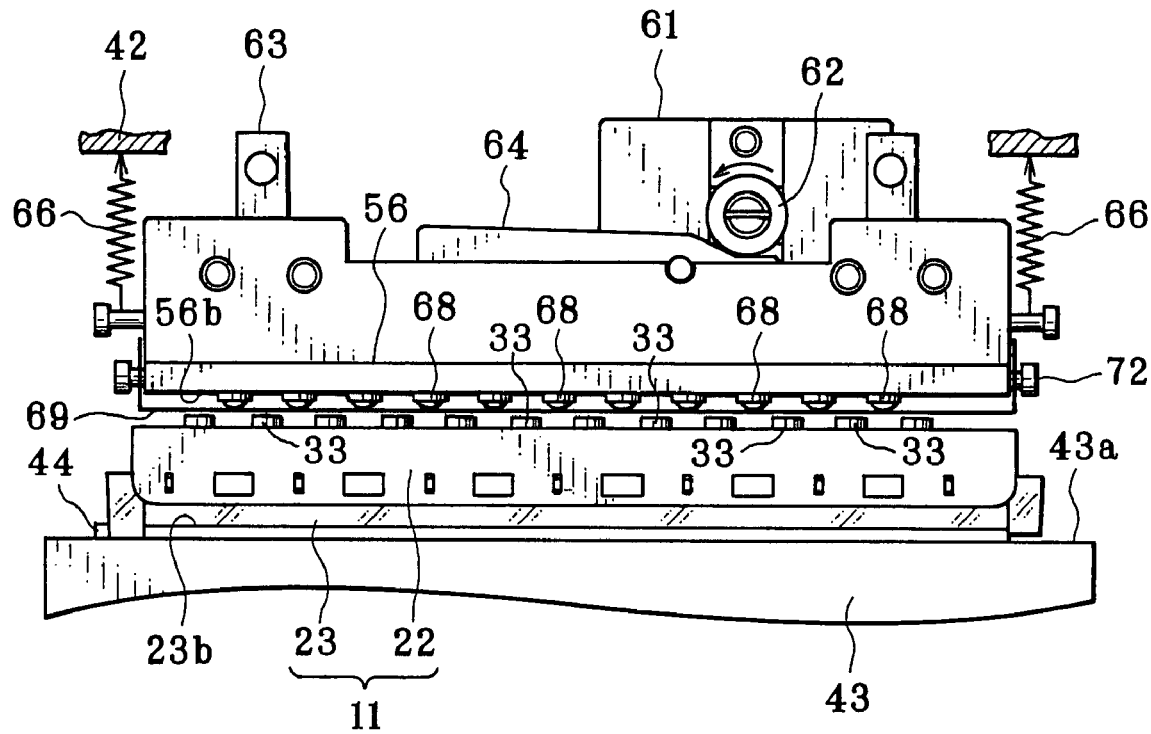
FIG. 5 is a side elevation illustrating a flow cell holder in an upper position.
Figure 6:
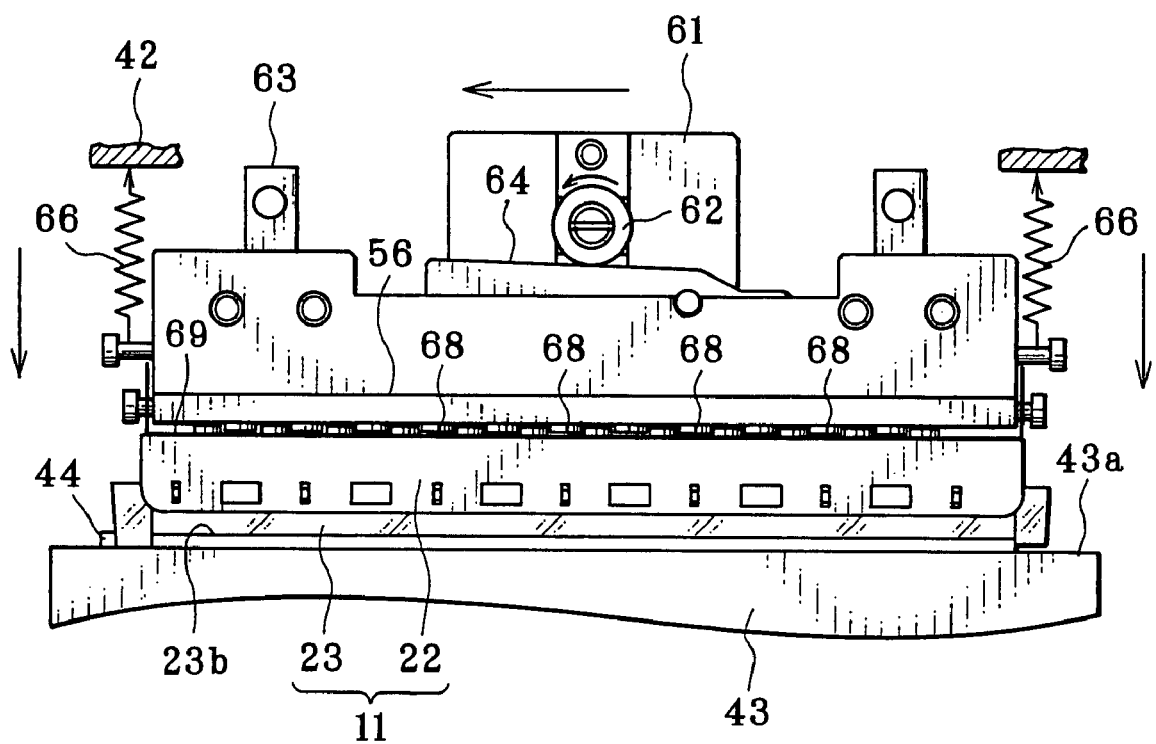
FIG. 6 is a side elevation illustrating the flow cell holder in a retaining position.

In FIGS. 5 and 6, the pad panel support 63 has the cam surface 64 engageable with the rotatable cam wheel 62. Bias of the tension coil springs 66 causes the cam surface 64 to contact the cam wheel 62. The cam surface 64 is inclined, and upon slide of the cam wheel 62 in the horizontal direction, causes the pad panel support 63 to move up or down according to the inclination. A height of the cam surface 64 increases from the right side to the left side. In FIG. 6, the cam wheel 62 slides to the left to push down the pad panel support 63 along the Z axis against the bias of the tension coil springs 66. In response to this, the pad panel 56 shifts to the retaining position. In contrast, when the cam wheel 62 slides to the right, the tension coil springs 66 cause the pad panel support 63 to move up along the Z axis. The pad panel 56 moves back to the initial position of FIG. 5.

A lower surface 56b of the pad panel 56 is opposed to an upper face of the flow cell 22. Spring plungers 68 or cushion plungers are disposed on the lower surface 56b. A resilient cushion panel 69 with a small thickness is located between the flow cell 22 and the spring plungers 68, and is an intermediate spacer with which the spring plungers 68 push the flow cell 22. Insertion holes 56c are formed in the pad panel 56, and receive insertion of the spring plungers 68, of which lower ends project from the lower surface 56b. The insertion holes 56c are arranged in two arrays and in the direction to follow arrangement of the insertion holes 56a. The spring plungers 68 in the insertion holes 56c are opposed to edge portions of the flow cell 22 as viewed in the width direction. Intervals of the spring plungers 68 are equal to one another in order to exert regularized force of cushion in the longitudinal direction of the flow cell 22.

The spring plungers 68 or cushion plungers are a known device and include the plunger body, the spring and the case. The spring biases the plunger body. The case is cylindrical, contains the plunger body and the spring, and keeps the plunger body movable in a direction of the biasing of the spring. The plunger body when in a first position is biased to advance from the case by the spring. A distal end of the plunger body is located outside the case. The plunger body is shiftable from the first position to a second position inside the case at a predetermined region of stroke. An example of the shape of the plunger body is a bullet shape. Note that a type of the spring plungers 68 may be a ball plunger of which the plunger body is spherical.

It is likely that an upper surface of the flow cell 22 comes to have a small distortion due to relatively low flatness according to the problem of the precision in molding. Should the lower surface 56b of the pad panel 56 be caused directly to contact the upper surface of the flow cell 22, stress or force may concentrate due to the distortion. The flow cell 22 cannot be pressed in a regularized manner. In view of this, the spring plungers 68 or cushion plungers are used to press the flow cell 22, to absorb local distortion of the upper surface of the flow cell 22 owing to stroke of the plunger bodies. Concentration of pressing force can be prevented even with the small distortion. Ends of the flow cell 22 in the width direction can be pressed in a regularized manner in the longitudinal direction.

Should the spring plungers 68 or cushion plungers contact the flow cell 22 directly, points of the contact of the flow cell 22 receive concentrated force. Thus, the cushion panel 69 is inserted between the spring plungers 68 and the flow cell 22, and converts the contact of points into contact of a surface.

The cushion panel 69 is a panel of metal having resiliency. Force of pushing of the spring plungers 68 or cushion plungers can be dispersed by the cushion panel 69, which are pressed by the spring plungers 68 to press the flow cell 22 without contact between the flow cell 22 and the spring plungers 68. This is effective in absorbing the upper distortion of the flow cell 22 at the same time as force of pressing can be regularized in the longitudinal direction of the flow cell 22.

Figure 7:
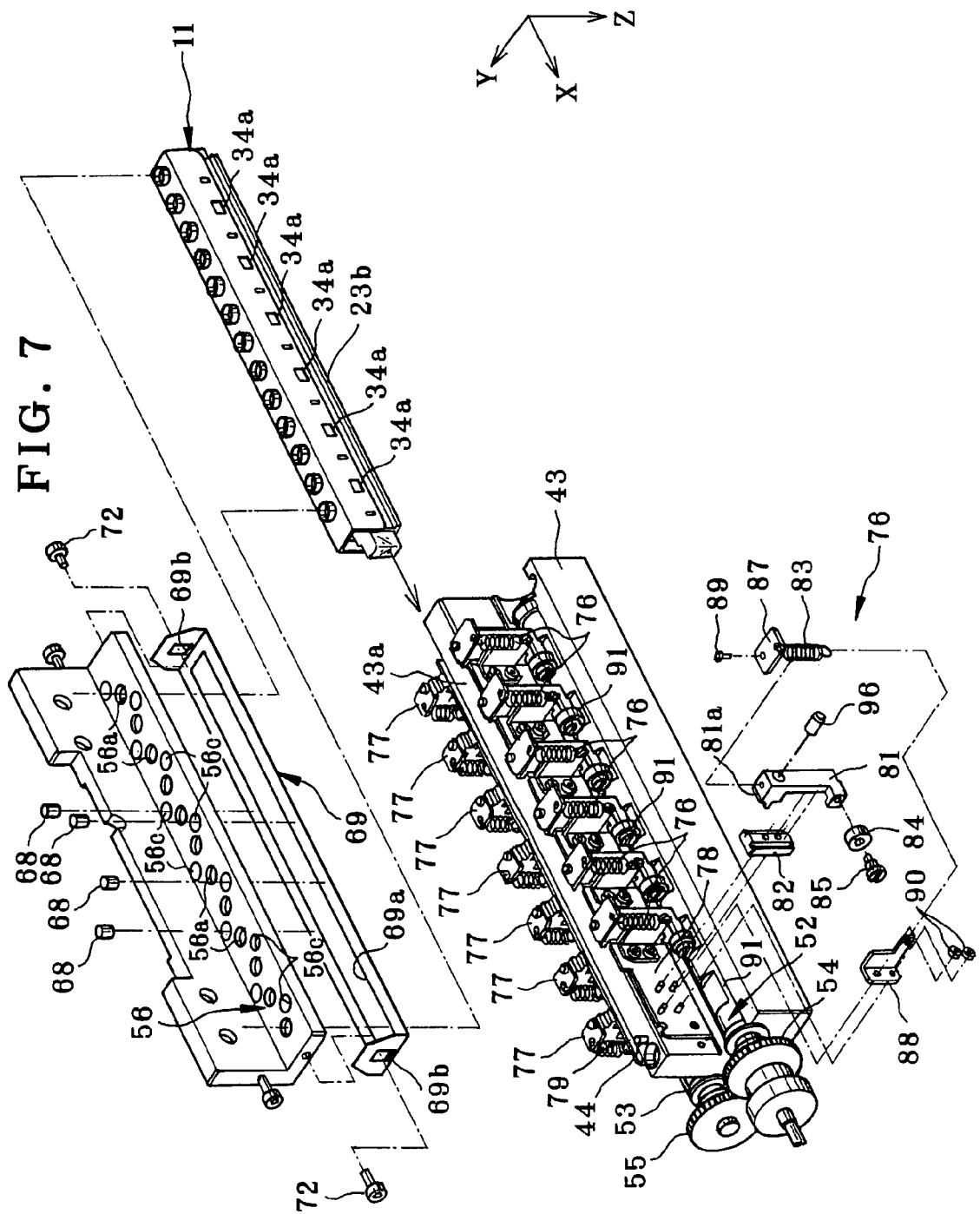
FIG. 7 is a perspective view illustrating a prism retaining mechanism.

In FIG. 7, a frame opening 69a is formed in the cushion panel 69 and extends in its longitudinal direction between panel ends which are opposed to the spring plungers 68 or cushion plungers. The pipette devices 16 access to the flow cell 22 through the frame opening 69a as a path.

Ends of the cushion panel 69 in the longitudinal direction are bent toward the ends of the pad panel 56. Engageable holes 69b are formed in the bent portions. Bolts 72 on the pad panel 56 are inserted in the engageable holes 69b. When the pad panel 56 is in the upper position, the inside of the engageable holes 69b of the cushion panel 69 is engaged with the bolts 72 to suspend the cushion panel 69 from the pad panel 56. Thus, the cushion panel 69 is movable up and down together with the pad panel 56.

The engageable holes 69b have such a size vertically greater than a diameter of the bolts 72 that, even while the bolts 72 are inserted in the engageable holes 69b, the cushion panel 69 can shift up or down. An interval between the cushion panel 69 and the lower surface 56b of the pad panel 56 changes between a state of the pad panel 56 in the home position of FIG. 5 and a state of the pad panel 56 in the retaining position of FIG. 6. Thus, shift of the spring plungers 68 or cushion plungers is ensured even in the presence of the cushion panel 69.

In FIG. 5, the cushion panel 69 is suspended in engagement with the bolts 72 while the pad panel 56 is in the upper position. A distance from the cushion panel 69 to the lower surface 56b is increased. A space of shifting tips of the spring plungers 68 or cushion plungers is ensured, so the spring plungers 68 can advance without blocking of the cushion panel 69. Stroke of retraction can be ensured. Then the pad panel 56 of the upper initial position starts moving down toward the retaining position. At first the cushion panel 69 contacts the flow cell 22. Although the moving down of the cushion panel 69 is completed, the pad panel 56 still continues moving down with a decrease in the distance to the cushion panel 69, because the size of the engageable holes 69b is greater than the diameter of the bolts 72. The flow cell 22 is pressed by the spring plungers 68 with the cushion panel 69 while tips of the spring plungers 68 become contained in their cases.

The prism retaining mechanism 46 includes plural first retaining units 76 and plural second retaining units 77 so positioned that the stage surface 43a is located between the arrays of the retaining units 76 and 77. The retaining units 76 and 77 are secured to lateral faces of the rack or stage platform 43. The retaining units 76 and 77 are arranged at a regular interval in the longitudinal direction of the sensor unit 11. When the sensor unit 11 is set on the stage surface 43a, the retaining units 76 and 77 are opposed to lateral faces of the prism 23. The retaining units 76 and 77 are engaged with the engageable ridges 23b of the prism 23 on sides in the width direction of the prism 23.

To ensure light paths to the sensor cells 27 with six combinations of channels in the sensor unit 11, the retaining units 76 and 77 are offset from the path openings 34a for passage of light. The numbers of the retaining units 76 and 77 are seven. Five of the first retaining units 76 are disposed between the path openings 34a. Remaining two of the first retaining units 76 are disposed at ends of the array of the path openings 34a. This is the same for the second retaining units 77.

Any of the retaining units 76 and 77 arranged longitudinally is discretely shiftable. Strain or distortion, if created in the engageable ridges 23b of the prism 23 in the longitudinal direction, can be absorbed by the combined use of the retaining units 76 and 77 with different stroke in the manner similar to the spring plungers 68 or cushion plungers. In the embodiment, the number of the first retaining units 76 is seven. However, the number of the first retaining units 76 may be at least two, which can be positioned at ends in the longitudinal direction. Similarly, the number of the second retaining units 77 may be at least two. The numbers of the retaining units 76 and 77 can be suitably determined in consideration of the number of the path openings 34a, the length of the sensor unit 11 or the like.

Support panels 78 and 79 are disposed to support the retaining units 76 and 77, which are positioned on lateral faces of the rack or stage platform 43. A plurality of combinations of bolts and nuts are used to fasten the support panels 78 and 79. Upper edges of the support panels 78 and 79 are higher than the stage surface 43a. When the sensor unit 11 is transferred in the direction of the X axis, the support panels 78 and 79 contact the engageable ridges 23b of the prism 23 to guide movement of the sensor unit 11 as guide rails.

Each of the first retaining units 76 includes a first holder or pusher 81, a holder rail 82, and a tension coil spring 83. The first holder 81 contacts a first one of the engageable ridges 23b for retention with force in the direction of the Z axis with pressure. The holder rail 82 is secured to the support panel 78 and keeps the first holder 81 movable up and down in the direction of the Z axis. The tension coil spring 83 respectively biases the first holder 81 toward the retaining position. The first holder 81 is movable between a retaining position and an upper initial position, and when in the retaining position, presses the engageable ridge 23b, and when in the upper position, releases the engageable ridge 23b from pressure. A tongue or pushing end 81a protrudes from an upper position of the first holder 81 toward a position higher than the stage surface 43a. In an initial state, the pushing end 81a is positioned higher than the engageable ridge 23b of the prism 23. A pressing surface of the pushing end 81a is parallel with an upper surface of the engageable ridge 23b, and when the first holder 81 moves down, contacts and presses the engageable ridge 23b. Then the prism 23 is pressed against the stage surface 43a.

A cam follower 84 is secured to a lower portion of the first holder 81 by a bolt 85 for contact with the cam shaft 52. An example of the cam follower 84 is a ball bearing, of which a rotational direction is set equal to a rotational direction of the cam shaft 52. The first holder 81 is slidable on the holder rail 82, and is likely to change in its orientation with influence of external force. However, the use of the ball bearing for the cam follower 84 reduces friction between the cam shaft 52 and the cam follower 84. Changes in the orientation of the first holder 81 can be suppressed in rotation of the cam shaft 52. Thus, the pushing end 81a of the first holder 81 can be kept suitably positioned with the engageable ridge 23b of the prism 23. Torque for driving the cam shaft 52 can be reduced by the reduction of the friction.

A panel or end connector 87 is connected with a first end of the tension coil spring 83. A piece or end connector 88 is connected with a second end of the tension coil spring 83. A bolt 89 fastens the end connector 87 to the upside of the first holder 81. Also, a bolt for the support panel 78 is inserted in the end connector 88. A nut 90 is helically engaged with the bolt for securing the end connector 88.

A cam surface 91 is formed on the cylindrical faces of the cam shaft 52, and positioned in association with the cam follower 84 of the first retaining units 76. The cam follower 84 is engaged with the cam surface 91, which drives the first retaining units 76 in response to rotation of the cam shaft 52.

Figure 8:
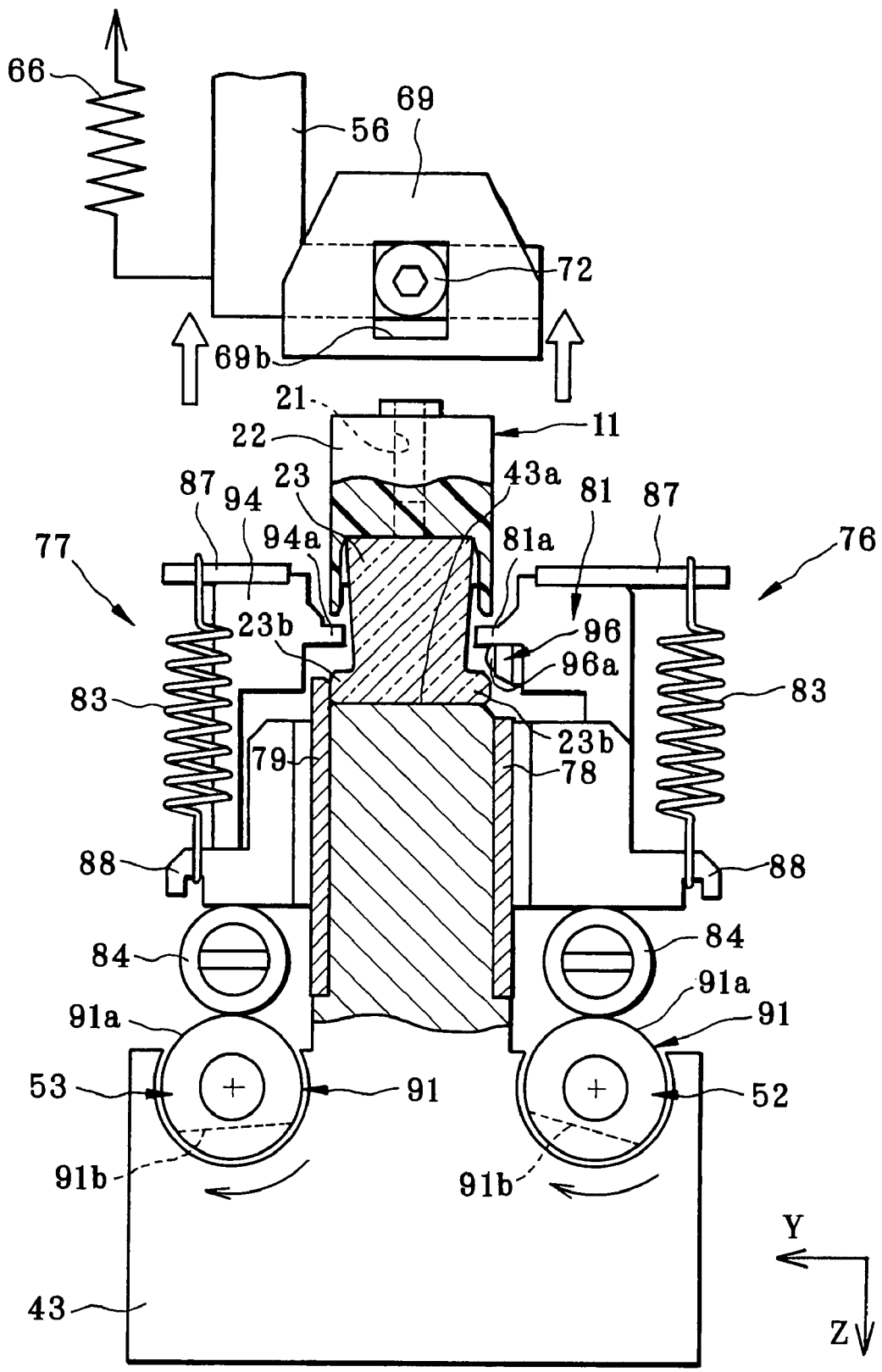
FIG. 8 is an explanatory view illustrating the prism retaining mechanism in an upper initial position.
Figure 9:
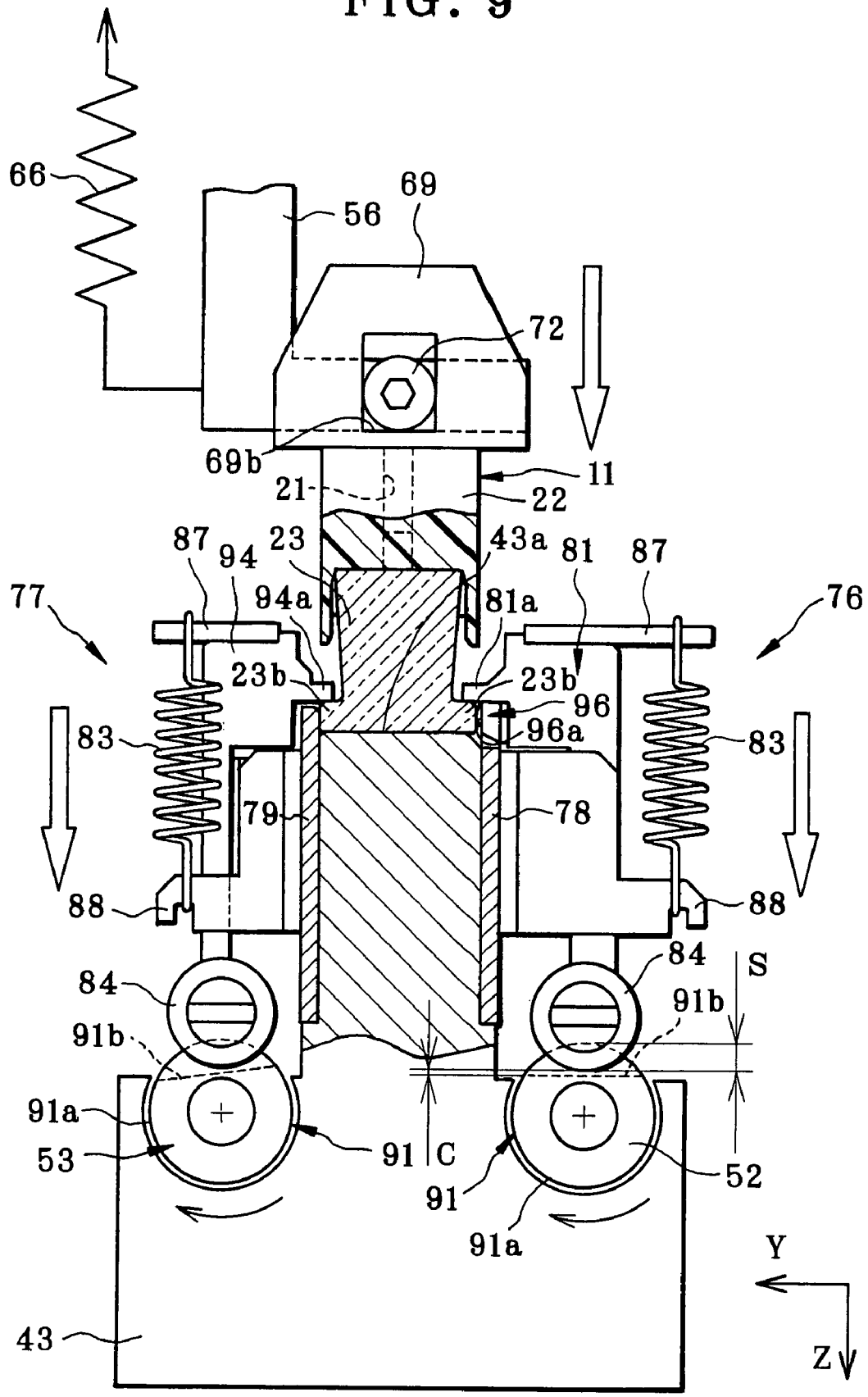
FIG. 9 is an explanatory view illustrating the prism retaining mechanism in a retaining position.

In FIGS. 8 and 9, each of the second retaining units 77 is structurally the same as the first retaining units 76, and includes a second holder or pusher 94, the tension coil spring 83 and the end connectors 87 and 88. The second holder 94 is a counterpart of the first holder 81. A tongue or pushing end 94a projects from the second holder 94 in the manner of the pushing end 81a. The cam follower 84 of the second holder 94 contacts the cam surface 91 of the cam shaft 53.

The cam surface 91 is in a D shape as viewed in a cross section and in a manner obtained by partially cutting a rod form. A curved section 91a and a flat section 91b are included in the cam surface 91. The cam surface 91 contacts the cam follower 84 to shift the first and second holders 81 and 94 in the direction along the Z axis. In FIG. 8, the cam surface 91 keeps the first and second holders 81 and 94 in an upper initial position against the tension coil spring 83 while the curved section 91a is positioned on the cam follower 84.

When the cam shaft 52 starts rotating in the clockwise direction, the flat section 91b of the cam surface 91 starts being opposed to the cam follower 84. The first and second holders 81 and 94 are started to move down in the direction of the Z axis by the tension coil spring 83. When the flat section 91b extends horizontally, the first and second holders 81 and 94 come to the retaining position which is the lower limit position. The cam shaft 52 further rotates, so the cam follower 84 becomes opposed to the curved section 91a. The first and second holders 81 and 94 move back to the initial position of FIG. 8.

A clearance C is created between the cam follower 84 and the flat section 91b in the reading position for preventing the flat section 91b from contacting the cam follower 84. It is possible to convert the bias of the tension coil springs 83 to force of retention along the Z axis efficiently, because the first and second holders 81 and 94 are suspended with the tension coil springs 83 in the retaining position. Force of biasing of each one of the tension coil springs 83 is approximately 500 gf. An amount S of stroke of shifting the first and second holders 81 and 94 with the tension coil springs 83 between the initial position and retaining position is approximately 1.5 mm. The clearance C is approximately 0.2-0.3 mm.

A phase of rotation of the cam shaft 52 is in advance of that of the cam shaft 53. Holding of the first holder 81 is started earlier than that of the second holder 94. This is because holding in the direction of the Y axis is started earlier than that in the direction of the Z axis. The phase of rotation of the cam shafts 52 and 53 is adjustable by adjusting the angle of positioning. In the embodiment, the cam shafts 52 and 53 are in a shape of a letter D. However, their shape as viewed in the section may be other forms, for example an ellipse, an oval, or the like with eccentricity.

A horizontal ball plunger 96 as horizontal holder or pusher is secured to the first holder 81 for supporting and positioning the lateral face of a first one of the engageable ridges 23b in the direction of the Y axis. The ball plunger 96 includes a ball 96a or plunger body, a compression spring, and a case. A compression spring biases the ball 96a. The case contains the ball 96a and the compression spring. The ball 96a is contained in a rotatable manner about its center.

The ball plunger 96 is secured to the inside of a hole disposed under the pushing end 81a in a direction to set the ball 96a on a lateral face of the engageable ridge 23b. In FIG. 8, the ball 96a of the ball plunger 96 protrudes upwards from the engageable ridge 23b when the first holder 81 is in the initial position.

In FIG. 9, the first holder 81 starts moving down to the retaining position. At first, the ball 96a contacts an upper edge of the engageable ridge 23b. A cutout is formed in an upper portion in the position of the ball plunger 96. When the cam surface 91 moves down further, the ball 96a comes into the cutout. The ball plunger 96 becomes contained in the case in contact with a curved surface of the engageable ridge 23b, until the ball plunger 96 contacts a face in the engageable ridge 23b. Then the ball plunger 96 starts pressing in the direction of the Y axis with the bias of the spring.

As the ball plunger 96 is secured to the first holder 81 for retention in the Z direction, the first holder 81 can move together with the ball plunger 96. So the structure can be simplified, because no specialized driving mechanism is required for the ball plunger 96.

The use of the ball plunger 96 is effective in preventing the engageable ridge 23b from being abraded in contact with the ball plunger 96. Specifically, the ball 96a is rotatable during a shift from the upper face of the engageable ridge 23b to its lateral face. Only a small friction occurs between the engageable ridge 23b and the ball plunger 96, to reduce possibility of abrading the engageable ridge 23b. Dust of scratch or abrasion can be also prevented. Although the use of the ball plunger 96 is effective, it is still possible to use a spring plunger for retention in the direction of the Y axis in which a plunger body is not rotatable.

The support panel 79 is disposed on the opposite side to the ball plunger 96 as viewed with respect to the stage surface 43a. An inner surface of the upper edge of the support panel 79 is a reference surface for positioning with respect to the Y axis. The ball plunger 96 presses a first lateral surface of the engageable ridge 23b. A second surface of the engageable ridge 23b opposite to the first lateral surface is pressed to the upper edge of the support panel 79. Accordingly, the prism 23 is positioned and retained in the direction of the Y axis. As the ball plunger 96 is disposed under the pushing end 81a, the ball plunger 96 starts contacting the engageable ridge 23b earlier than the pushing end 81a while the first holder 81 moving down. Thus, holding in the direction of the Y axis starts before the start of that of the Z axis.

The first and second holders 81 and 94 are disposed in consideration of the position of the prism 23 in the retention along the Y axis. It is likely immediately after the handling with the handler 41 that the sensor unit 11 is inclined or offset from the target position. So retention in the direction of the Y axis is carried out earlier than retention in the direction of the Z axis. The latter can be carried out appropriately.

The second holder 94 starts retaining the prism 23 along the Z axis after the start of retention with the first holder 81 along the Z axis with a slight delay at a phase difference between the cam shafts 52 and 53. To release the prism 23 from the retention, the motor 51 rotates in a backward direction. The second holder 94 starts moving earlier according to the phase difference, before the first holder 81 starts moving. The pushing end 81a shifts away from the first one of the engageable ridges 23b upon the start of moving the first holder 81. Then the ball plunger 96 moves away from the engageable ridge 23b upon further movement of the first holder 81, to release the engageable ridge 23b in the direction along the Y axis. The ball 96a of the ball plunger 96 comes away from the engageable ridge 23b during contact with the engageable ridge 23b. Friction of the ball plunger 96 exerts force to the prism 23 for an inclination rotational about the X axis. However, the flow cell holder 47 continues pressing even during the release of the retention of the prism retaining mechanism 46. The sensor unit 11 is prevented from being inclined.

Although the second holder 94 starts moving earlier than the first holder 81 to release the prism 23, it is possible in the invention to start moving the first holder 81 earlier than the second holder 94. This is effective in suppressing changes in the orientation of the sensor unit 11 because the second holder 94 continues to retain the prism 23 upon the start of frictional engagement of the ball plunger 96 with the first engageable ridge 23b in moving the first holder 81.

The sensor unit 11 is held by the flow cell holder 47 and the prism retaining mechanism 46. In holding of the flow cell holder 47, the flow cell 22 is an intermediate element, and also has resiliency and is softer than the prism 23. If force is applied to the sensor unit 11 by loading and unloading of the pipette devices 16, orientation or position of the sensor unit 11 is likely to occur due to deformation of the flow cell 22 held by the flow cell holder 47. However, the prism retaining mechanism 46 is combined with the flow cell holder 47, and is directly engaged with the prism 23 which is more rigid than the flow cell 22. The sensor unit 11 can be held reliably.

Figure 10:
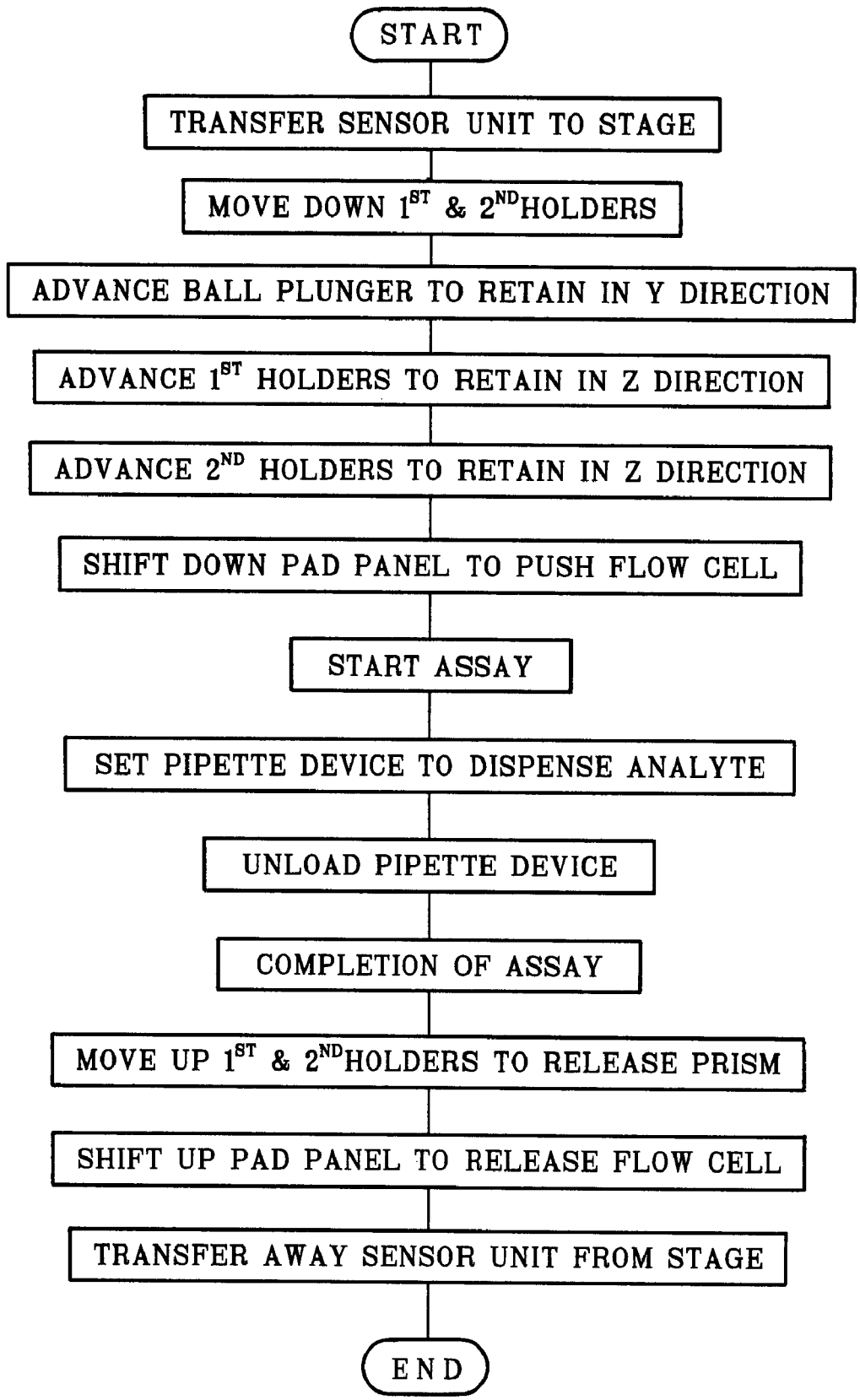
FIG. 10 is a flow chart illustrating holding and release of the sensor unit.

The operation of the embodiment is described by referring to the flow in FIG. 10. At first before an assay, the sensor unit 11 is handled and transferred by the handler 41 in the direction of the axis X, and is set on the assay stage 14. The sensor unit 11 on the assay stage 14 is guided by the support panels 78 and 79 for the movement. In the transfer of the sensor unit 11, the prism retaining mechanism 46 and the flow cell holder 47 are in the initial position of FIG. 8. The sensor unit 11 can be smoothly moved without contact between the prism 23 and any of the pushing ends 81a and 94a and the ball plunger 96. When the sensor unit 11 comes to the position to contact the stopper 44, the transfer in the direction along the X axis is stopped.

When the sensor unit 11 is set on the stage surface 43a, the controller 40 actuates the prism retaining mechanism 46 and the flow cell holder 47 of the initial position of FIG. 8, to set the sensor unit 11 in the predetermined position and orientation.

At first, the controller 40 causes the motor 51 to rotate the cam shafts 52 and 53. Driving of the first and second holders 81 and 94 is started. The cam surface 91 rotates. When the contact of the flat section 91b with the cam follower 84 starts after the contact of the curved section 91a with the cam follower 84, the first and second holders 81 and 94 start moving down to the retaining position by the bias of the tension coil springs 83. Owing to the use of the ball bearing in the cam follower 84, the first and second holders 81 and 94 can be moved down with small friction between the cam follower 84 and the cam surface 91.

When the first holder 81 starts moving down, at first the ball plunger 96 contacts the upside of the first engageable ridge 23b. The ball 96a shifts down inside the ball plunger 96 and simultaneously comes to a lateral face of the engageable ridge 23b. The engageable ridge 23b is pressed in the direction along the Y axis to press the prism 23 toward the support panel 79. The prism 23 is retained and positioned in the direction of the Y axis. As there is small friction between the ball plunger 96 and the engageable ridge 23b, no scratch occurs on the engageable ridge 23b. Also, holding of the prism 23 can be started without occurrence of an inclination.

When the first holder 81 moves down, the pushing end 81a contacts the first engageable ridge 23b to start retention in the direction of the Z axis. Slightly later than the first holder 81, the pushing end 94a of the second holder 94 contacts the second engageable ridge 23b for retention in the same direction. As retention in the direction of the Y axis has been started, the retention in the direction of the Z axis can be started in stable orientation of the prism 23.

When the prism retaining mechanism 46 firmly retains the prism 23, the controller 40 causes the motor 58 to rotate to move down the pad panel 56 to the retaining position. Upon moving down of the pad panel 56, the cushion panel 69 contacts the flow cell 22 to press the flow cell 22 on the prism 23. As the flow cell 22 is pressed by the contact of the spring plungers 68 or cushion plungers and the cushion panel 69, the pad panel 56 can operate to apply pressure in a uniform manner. Also, the sensor unit 11 can be stable without an inclination or fall, as retention with the flow cell holder 47 is started after retention with the prism retaining mechanism 46.

After the operation for retaining the sensor unit 11, assay is started. The pipette devices 16 access to the flow channel 21 simultaneously, to dispense and aspirate fluid in the flow channel 21. SPR signals from the sensor cells 27 are obtained simultaneously. As the pipette devices 16 are inserted at the same time, relatively high force is exerted to the sensor unit 11. However, the sensor unit 11 can be retained by the flow cell holder 47 and the prism retaining mechanism 46. No change in orientation or the position of the sensor unit 11 will occur.

Reading of the SPR signal is started before insertion of the pipette devices 16, and continues even after removal of the pipette devices 16. The sensor unit 11 is kept appropriately oriented in any steps of the reading, so the assay can be carried out precisely.

After the assay, the controller 40 rotates the motor 51 to shift the prism retaining mechanism 46 for releasing. The flow cell holder 47 still continues the retention, the sensor unit 11 can be stable in the orientation even upon the release of the prism retaining mechanism 46. After this, the pad panel 56 moves up, to shift the flow cell holder 47 for releasing. Then the handler 41 handles and transfers the sensor unit 11 away from the assay stage 14. The sensor unit 11 is kept oriented suitably even after releasing of the retention. The squeezed state of the sensor unit 11 in the handler 41 can continue. No failure will occur in transfer of the sensor unit 11, as the sensor unit 11 can be prevented from dropping down from the handler 41.

Figure 11:
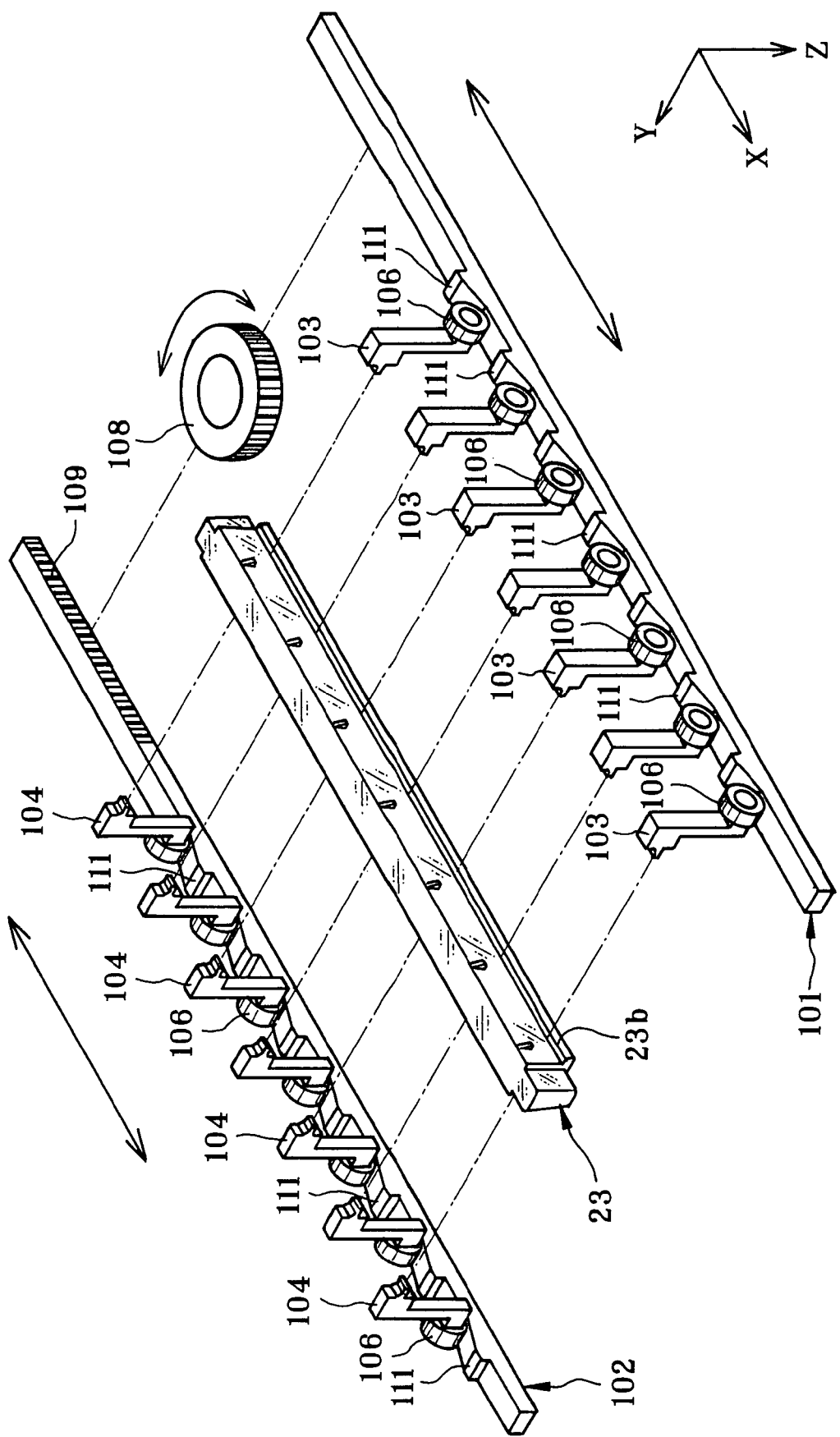
FIG. 11 is a perspective view illustrating a driving mechanism for a holder or pusher in which a cam plate is used.
Figure 12:
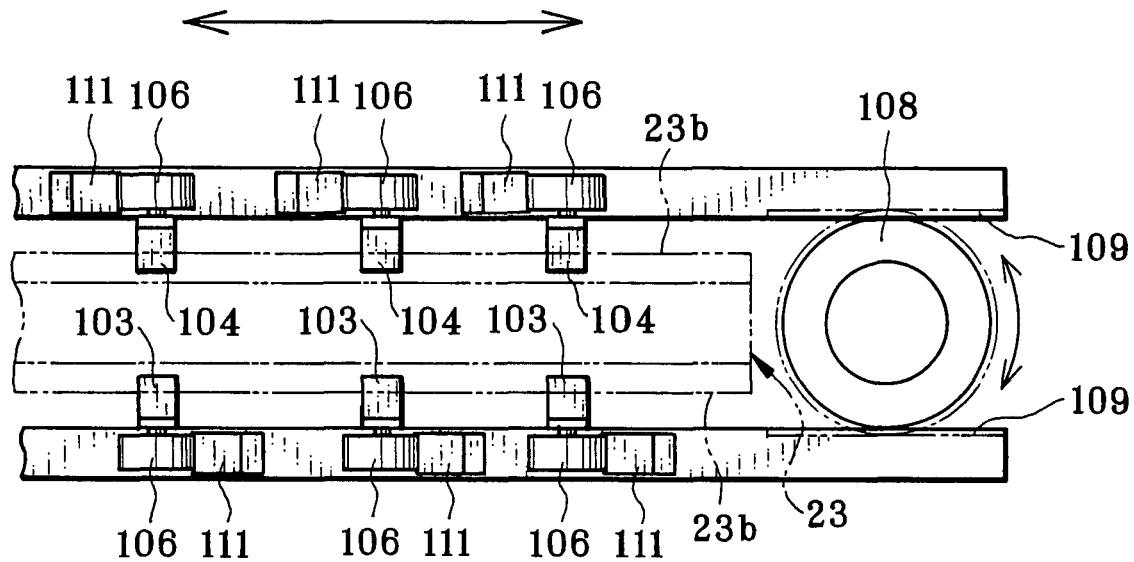
FIG. 12 is a plan illustrating the driving mechanism.
Figure 13:
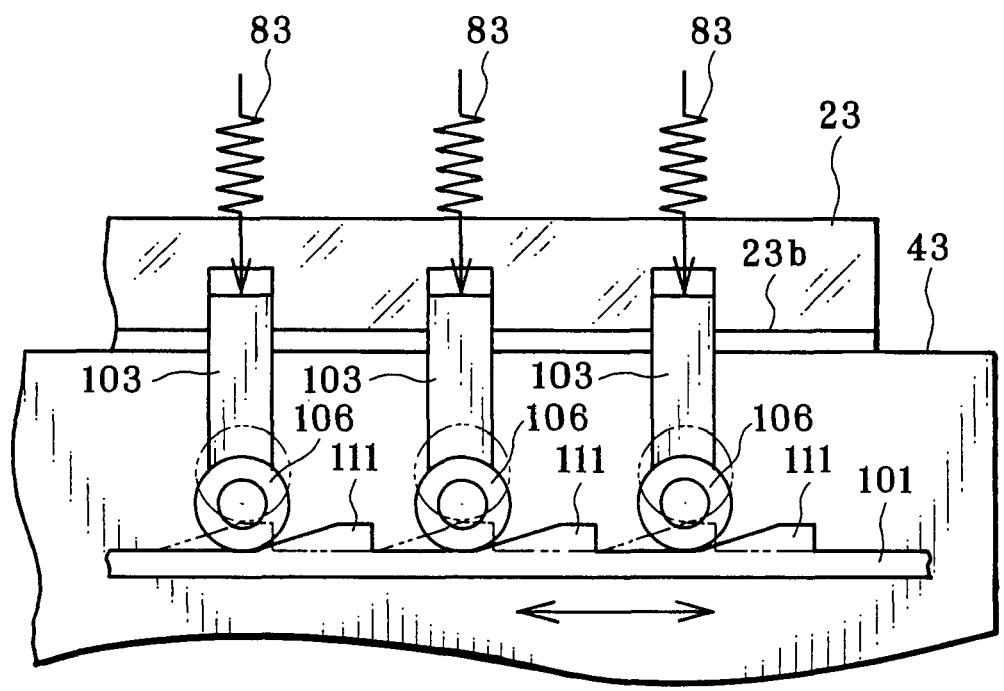
FIG. 13 is a side elevation illustrating the driving mechanism.

In contrast to the above embodiment having the cam shafts, another preferred embodiment is illustrated in FIGS. 11-13, in which cam plates 101 and 102 are used. First holders or pushers 103 are arranged beside the prism 23 in its longitudinal direction. Second holders or pushers 104 are opposed to the first holders 103 on the opposite side relative to the prism 23. Pushing ends or projections are formed with an upper portion of the first and second holders 103 and 104. A cam follower 106 is disposed on each lower portion of the first and second holders 103 and 104 for engagement with the cam plates 101 and 102.

The cam plate 101 longitudinally extends in the array direction of the first holders 103, and slides in the same direction or along the X axis. The first holders 103 are moved up and down along the Z axis by the cam plate 101. Also, the cam plate 102 longitudinally extends in the array direction of the second holders 104, and slides in the same direction or along the X axis. The second holders 104 are moved up and down along the Z axis by the cam plate 102.

A rack gear 109 is formed on a surface of each of the cam plates 101 and 102. A pinion 108 is meshed with the rack gear 109. When the pinion 108 rotates, the cam plates 101 and 102 slide in the direction of the X axis. In FIG. 12, the cam plates 101 and 102 slide in the directions opposite to one another. When the pinion 108 rotates in the clockwise direction, the cam plate 101 slides to the left, the cam plate 102 sliding to the right. A motor causes the pinion 108 to rotate to drive the cam plates 101 and 102.

A cam surface 111 is formed on each of the cam plates 101 and 102 for engagement with the cam follower 106. In FIG. 13, the cam surface 111 in the cam plate 101 is constituted by a surface of a plurality of wedge shaped projections, and positioned at the cam follower 106. The cam surface 111 has an inclined section and a flat section. The first holders 103 are biased down by the tension coil springs 83, and are moved up and down by slide of the cam surface 111. The contact of the flat section of the cam surface 111 with the cam follower 106 is indicated by the phantom line for an initial position. When the cam plate 101 slides to the right, the first holders 103 move down to the retaining position by an inclined form of the inclined section. Upon the slide of the cam plate 101 to the right, the cam surface 111 moves up the first holders 103 against the tension coil springs 83, to move back to the initial position from the retaining position.

Note that the cam follower 106 and the cam surface 111 can be preferably disposed with ensured clearance between those for the purpose of applying force of bias of the tension coil springs 83 to the first holders 103 fully at 100% in the retaining position.

An example of the cam follower 106 is a ball bearing, of which a rotational direction is determined to follow a sliding direction of the cam plate 101. The use of the ball bearing for the cam follower 106 reduces friction between the cam plate 101 and the cam follower 106. Changes in the orientation of the first holders 103 can be suppressed in rotation of the cam plate 101. Force for driving the cam plate 101 can be reduced by the reduction of the friction.

The use of the cam plates is compared with that of the cam shafts. As a result of calculation to simulate, force of driving by use of the cam plates is smaller. Seven holders on a first side and seven holders on a second side are shifted while biased by a spring mechanism at a force of 500 gf. Calculated torque of driving of the cam shaft is approximately 3.4 kgf.cm. In contrast, calculated torque of the pinion driving of the cam plate is approximately 1.28 kgf.cm.

In a manner similar to the cam plate 101, the cam surface 111 is formed on the cam plate 102, and drives the second holders 104. For the cam plate 102 to slide in a direction opposite to that of the cam plate 101, an inclination of the cam surface 111 on the cam plate 102 is reverse to an inclination of the cam surface 111 on the cam plate 101.

In the above embodiment, the engageable ridges 28 and 92 are protrusions. However, engageable portions for engagement with a holder or pusher may be engageable channels in place of the ridges. In the above embodiment, a shape of the ridges as viewed in a cross section is quadrilateral. However, a shape of the ridges as viewed in a cross section may be a quadrilateral with an upper inclination, a projecting shape in a curved form at the upper end, and the like.

In addition to the assay apparatus 10 of the above embodiment, an assay sensor unit according to the invention can be other sensors in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it is possible to measure the interaction on the sensing surface.

Unlike the above assay method in utilizing attenuated total reflection, an assay of the invention may be an assay with a sensor unit according to other methods in an optical manner. Optical blocks may be shaped in any one of various forms. Optical blocks of the invention may be an element different from a prism, for example a transparent plate. Material for optical blocks may be any transparent substance other than the resin, for example glass.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay apparatus comprising: a sensor unit including an optical block having a sensing surface, disposed on an upper surface thereof, for detecting reaction of a sample, and a flow cell, secured to said upper surface, having a flow channel for flow of sample fluid containing said sample to said sensing surface;
    a light source for applying light to said optical block;
    a detector for optically measuring reaction of said sample on said sensing surface, said assay apparatus further comprising:
    an assay stage, having a stage surface for contacting a lower surface of said optical block, for supporting said sensor unit removably;
    an optical block retaining mechanism for retaining said sensor unit in a predetermined orientation on said stage surface by engagement with a housing for said optical block;
    said optical block retaining mechanism including a holder, wherein said holder is shiftable between a retaining position and an initial position, wherein in said retaining position, said holder which pushes vertically on the housing to place said lower surface of said optical block on said stage surface, wherein in said initial position, said holder releases vertical force on the housing to release said optical block from retention on said stage surface.

2. An assay apparatus as defined in claim 1, further comprising a fluid dispenser having a pipette device;
    wherein said pipette device moves vertically to access to said flow cell, and introduces said sample fluid when set at said flow channel.

3. An assay apparatus as defined in claim 2, wherein plural sensing surfaces are arranged in said sensor unit in a sensor longitudinal direction, plural flow channels are arranged in said sensor unit and correspond to said sensing surfaces, and plural pipette devices of said fluid dispenser access to said flow channels.

4. An assay apparatus as defined in claim 3, said optical block retaining mechanism further comprising a biasing mechanism for biasing said holder toward said retaining position.

5. An assay apparatus as defined in claim 3, wherein said optical block includes first and second engageable portions formed to protrude from respectively lateral faces thereof;
    said holder is at least two holders so positioned that said stage surface is located between, for pushing an upper face of said first and second engageable portions in said vertical direction.

6. An assay apparatus as defined in claim 5, wherein said at least two holders are at least four holders arranged in first and second arrays extending in said sensor longitudinal direction thereof.

7. An assay apparatus as defined in claim 6, wherein said holders are shiftable independently from one another.

8. An assay apparatus as defined in claim 7, further comprising:
    a cam follower secured to said holder; and
    a cam for driving said cam follower to shift said holder.

9. An assay apparatus as defined in claim 8, wherein said cam includes a flat surface, wherein the flat surface is so disposed that the flat surface is in contact with said cam follower when said holder reaches said retaining position.

10. An assay apparatus as defined in claim 3, wherein said optical block retaining mechanism further comprises a horizontal holder for pushing a first lateral face of said optical block in a horizontal direction which is along said stage surface, to set a second surface of said optical block on a reference surface on said assay stage for holding in said horizontal direction.

11. An assay apparatus as defined in claim 10, wherein said sensor unit moves in said sensor longitudinal direction for transfer to said assay stage, and said sensor longitudinal direction is crosswise to said first direction and to said horizontal direction.

12. An assay apparatus as defined in claim 10, wherein said horizontal holder is supported on said holder, and starts retention in said horizontal direction together with said holder.

13. An assay apparatus as defined in claim 3, further comprising a flow cell holder for accessing downwards to said flow cell of said sensor unit on said stage surface, and for pushing an upper surface thereof to press said flow cell on said optical block.

14. An assay apparatus as defined in claim 13, wherein pushing of said optical block retaining mechanism and said flow cell holder is started after transfer of said sensor unit to said assay stage is completed.

15. An assay apparatus as defined in claim 13, further comprising a cushion mechanism placed between the flow cell holder and the flow cell for reducing shock between said flow cell holder and said flow cell at a time of pushing.

* * * * *